(12) United States Patent
Wallander (10) Patent No.: US 11,064,847 B2
(45) Date of Patent: Jul. 20, 2021

(54) TOWEL WARMING APPARATUS

(71) Applicant: James Joseph Wallander, Coppell, TX (US)

(72) Inventor: James Joseph Wallander, Coppell, TX (US)

( * ) Notice: Subject to any disclaimer, the term of this patent is extended or adjusted under 35 U.S.C. 154(b) by 0 days.

(21) Appl. No.: 16/651,289

(22) PCT Filed: Feb. 22, 2019

(86) PCT No.: PCT/US2019/019095
§ 371 (c)(1),
(2) Date: Mar. 26, 2020

(87) PCT Pub. No.: WO2019/165174
PCT Pub. Date: Aug. 29, 2019

(65) Prior Publication Data
US 2020/0375412 A1  Dec. 3, 2020

Related U.S. Application Data

(60) Provisional application No. 62/634,045, filed on Feb. 22, 2018.

(51) Int. Cl.
*A47K 10/06* (2006.01)
*A61M 21/00* (2006.01)
(Continued)

(52) U.S. Cl.
CPC .............. *A47K 10/06* (2013.01); *A61M 21/00* (2013.01); *D06F 59/02* (2013.01); *D06F 59/08* (2013.01);
(Continued)

(58) Field of Classification Search
CPC .......... A47K 10/06; A47K 10/10; F24H 3/02; F24H 9/2064; H04M 1/72415;
(Continued)

(56) References Cited

U.S. PATENT DOCUMENTS 2,668,368 A * 2/1954 Jacobs .................... A47K 10/06
34/621
3,475,828 A * 11/1969 Moscowitz ............. D06F 73/02
34/443
(Continued)

FOREIGN PATENT DOCUMENTS

JP  2015062673 A  *  4/2015
WO  2019165174 A1  8/2019
WO  WO-2019165174 A1 *  8/2019  ........... F24H 9/2064

OTHER PUBLICATIONS

Filing receipt and specification for provisional patent application entitled "Towel Warming Apparatus," by James Joseph Wallander, filed Feb. 22, 2018 as U.S. Appl. No. 62/634,045.

*Primary Examiner* — Stephen M Gravini
(74) *Attorney, Agent, or Firm* — Barnes & Thornburg LLP (57) ABSTRACT

Embodiments relate generally to a heated towel rack that includes at least one lateral support, at least one forced air heating unit in fluid communication with a channel within a lateral support, and at least one cross bar coupled to the at least one lateral support. The at least one cross bar including at least one vent that traverses into a conduit within the cross bar. The channel is in fluid communication with the at least one vent by way of the conduit.

16 Claims, 9 Drawing Sheets

(51) Int. Cl.
*D06F 59/02* (2006.01)
*D06F 59/08* (2006.01)
*F24H 3/02* (2006.01)
*F24H 9/20* (2006.01)
*A47K 10/10* (2006.01)
*H04M 1/72415* (2021.01)

(52) U.S. Cl.
CPC .............. *F24H 3/02* (2013.01); *F24H 9/2064* (2013.01); *A47K 10/10* (2013.01); *A61M 2021/0016* (2013.01); *H04M 1/72415* (2021.01)

(58) Field of Classification Search
CPC ........ D06F 59/02; D06F 59/08; A61M 21/00; A61M 2021/0016
USPC ............................................................. 34/239
See application file for complete search history.

(56) References Cited

U.S. PATENT DOCUMENTS

| | | | | |
|---|---|---|---|---|
| 4,094,076 | A * | 6/1978 | Baslow | A45D 20/12 219/521 |
| 5,642,462 | A * | 6/1997 | Huff | A47K 10/06 211/105.1 |
| 5,842,287 | A * | 12/1998 | Murphy | A47K 10/06 34/202 |
| 5,953,830 | A * | 9/1999 | Jannach | D06F 59/02 34/104 |
| 6,796,053 | B2 * | 9/2004 | Lurie | A47L 23/20 34/104 |
| 9,145,996 | B2 * | 9/2015 | Mendez | F16L 41/02 |
| 9,918,594 | B2 * | 3/2018 | Robertson | A47K 10/04 |
| 10,718,565 | B2 * | 7/2020 | Hinkey | F26B 21/006 |
| 2020/0375412 | A1 * | 12/2020 | Wallander | D06F 59/08 |

* cited by examiner

TOWEL WARMING APPARATUS

CROSS-REFERENCE TO RELATED APPLICATIONS

This application is a filing under 35 U.S.C. 371 of International Application No. PCT/US2019/019095 filed Feb. 22, 2019, which claims priority to U.S. Provisional Patent Application Ser. No. 62/634,045 filed Feb. 22, 2018 by James Joseph Wallander and entitled "Towel Warming Apparatus" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Using a warm and dry towel to dry oneself off is a comforting feeling and preferable alternative to a damp cold towel. In order to have readily available warm dry towels, some users utilize towel warmers. While these towel warmers provide some warmth, they do not evenly warm/dry towels and mostly heat the towel at the point of contact. Therefore, a need exists for an apparatus to evenly warm and dry a towel.

SUMMARY

In an embodiment, a garment drying rack may comprise at least one lateral support comprising a channel within the interior of the lateral support; at least one forced air unit in fluid communication with the channel within the lateral support configured to generate airflow into the channel; a plurality of cross bars comprising conduit positioned within the interior of the cross bars, wherein the conduit is in fluid communication with the channel; and a plurality of vents in fluid communication with the conduit, the channel being in fluid communication with the plurality of vents by way of the conduit.

In an embodiment, a method for assembling a towel drying rack may comprise connecting one or more lateral supports to a plurality of cross bars; fluidly connecting a channel within at least one of the lateral supports to conduit within each of the plurality of cross bars; fluidly connecting the conduit with a plurality of vents formed into the cross bars, wherein the vents are configured to direct airflow out of the towel drying rack; and fluidly connecting a forced air unit to at least one of the channel and the conduit.

In an embodiment, a heated towel rack may comprise at least two lateral supports; at least one forced air heating unit in fluid communication with a channel within a lateral support; a plurality of cross bars being coupled between the at least two lateral supports; each cross bar of the plurality of cross bars comprises a plurality of vents that traverse into a conduit within the cross bar; and the channel being in fluid communication with the plurality of vents by way of the conduit.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

In an embodiment of the disclosure, a heated towel rack is provided as an apparatus for heating and/or drying towels. The heated towel rack may comprise a plurality of cross bars vertically arranged between one or more lateral support structures that serve as the racks a user on which a user may be able to hang a towel or other garment. At least one cross bar of the plurality of cross bars may include at least one vent configured to evenly distribute heated (or non-heated) air to the towel or garment, allowing the towel or garment to be evenly warmed and/or dried. In some embodiments, a plurality of cross bars may comprise a plurality of vents.

In some embodiments, a heated towel rack may include one or more (in some embodiments, two) lateral supports, at least one forced air heating unit in fluid communication with at least one channel within a lateral support, and a plurality of cross bars coupled between the one or more lateral supports. At least one cross bar of the plurality of cross bars may include at least one vent that traverses into a conduit within the cross bar. The channel of the lateral support may be in fluid communication with the at least one vent by way of the conduit of the cross bar. In some configurations, the at least one cross bar may be rotatably coupled with the at least one lateral support. The rotatable coupling between the cross bar(s) and the lateral support(s) would allow for the rotation of individual cross bars allowing a user to direct the angle of the vent(s) in order to redirect forced heated air to their liking.

In some embodiments, the at least one forced air heating unit may include at least one heating element, a fan, and a controller. The controller may be operatively coupled to the at least one heating element and the fan in order to control air temperature and air flow through the vent(s).

In some embodiments, the heated towel rack may include a first lateral support and a second lateral support. The first lateral support and the second lateral support may be differentiated by the attachment of the forced air heating unit. For example, the first lateral support may be coupled to at least one forced air heating unit, while the second lateral support may lack any direct coupling to a forced air heating unit. In alternative embodiments, the at least one forced air heating unit may not be coupled to a lateral support and may be coupled to a support cross bar that is in fluid communication with the at least one cross bar. In some embodiments, the heated towel rack may include a stopper that is obstructively positioned within the conduit proximal to the second lateral support to prevent heated air to enter the channel of the second lateral support. In some embodiments, the conduit may taper towards the first lateral support, such that the width of the conduit as it approaches the second lateral support is wider than the width of the conduit near the first lateral support.

In some embodiments, the heated towel rack may be configured with at least two lateral supports that comprise a first section and a second section. The first section may be proximal to the at least one forced air heating unit. The second section may be distal to the at least one forced air heating unit. The conduits of the plurality of cross bars in the second section may be larger than plurality of vents in the first section to evenly distribute the airflow through the towel rack.

In some embodiments, the heated towel rack may include an attachable aroma therapy element comprising one or more of: a clip, a housing, at least one slot, and/or a scented compound. The scented compound may be positioned within the housing. The at least one slot may traverse through the housing. The attachable aroma therapy element may be configured to couple to a cross bar adjacent to a vent. The at least one slot may be operatively aligned with the vent in order to allow the scented compound to enter into the surrounding environment via the airflow directed out of the vent and therefore through the housing of the aroma therapy element.

In some embodiments, the heated towel rack may be configured with the at least one cross bar having a cylindrical shape (profile). Alternatively, the heated towel rack may be configured with the at least one cross bar having a rectangular shape (profile). In some embodiments, the heated towel rack may be configured with a plurality of cross bars having similar or dissimilar shapes for each of the cross bars, where a portion of the cross bars may be differently shaped than another portion of the cross bars.

Referencing FIG. 1 through FIG. 5, a heated towel rack 100 is an apparatus for drying and/or warming towels. A towel 102 placed on the rack receives heated air forced through a plurality of vents that help dry and heat a towel to a comfortable temperature. The heated towel rack 100 is configured to be mounted or attached to a surface (for example a counter or a wall), but alternative configurations may be provided that allow the towel rack to be a standing structure on the ground. The attachment to a wall may comprise adhesive, physical connectors, screws, nails, slots, and/or other connecting elements. In other embodiments, the towel rack may be freestanding and may function without being attached to a surface or wall.

Figure 2:
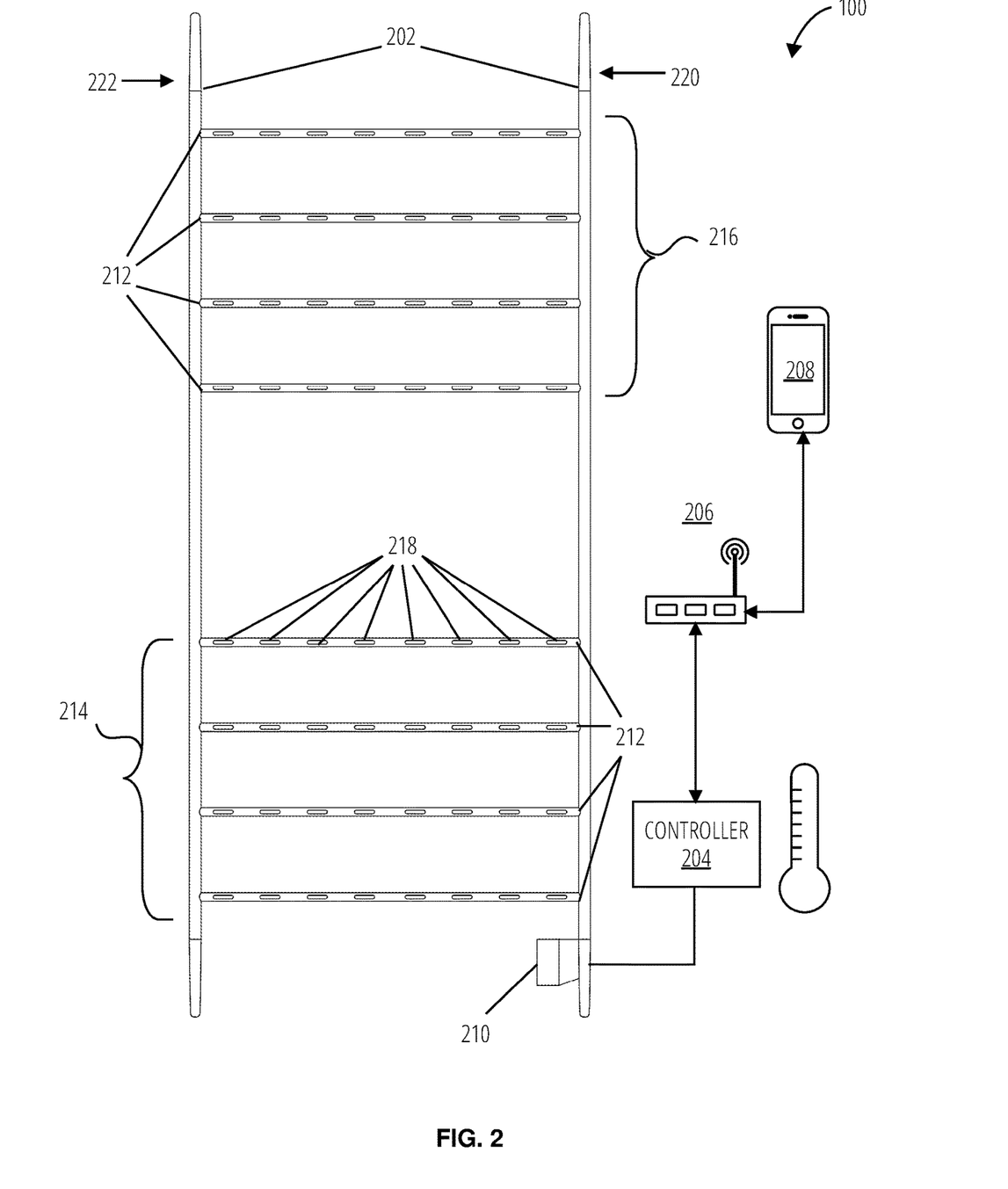
FIG. 2 illustrates a front view of the heated towel rack 100 in accordance with one embodiment.
Figure 3:
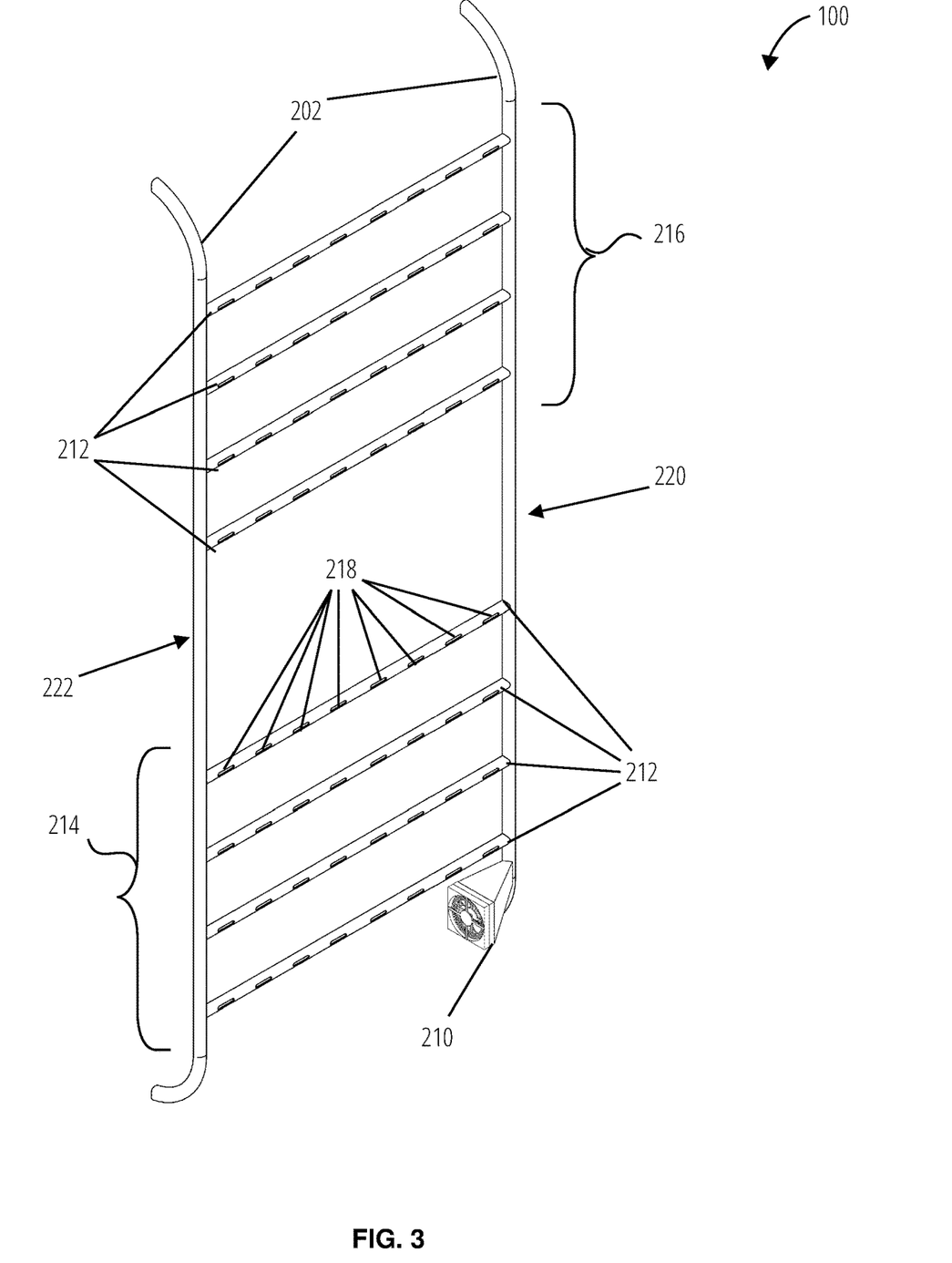
FIG. 3 illustrates an isometric view of the heated towel rack 100 in accordance with one embodiment.

Referring to FIG. 2, the heated towel rack 100 comprises an at least two lateral supports 202, a forced air heating unit 210, and a plurality of cross bars 212. The at least two lateral supports 202 are positioned parallel to one another and provide a support structure for the heated towel rack 100. In some embodiments, the lateral supports 202 may not be aligned parallel and may form a "V" shape and/or "A" shape. In some embodiments, the at least two lateral supports may be individually referenced as a first lateral support 220 and a second lateral support 222. In some embodiments, the towel rack 100 may only comprise a single lateral support.

Figure 4:
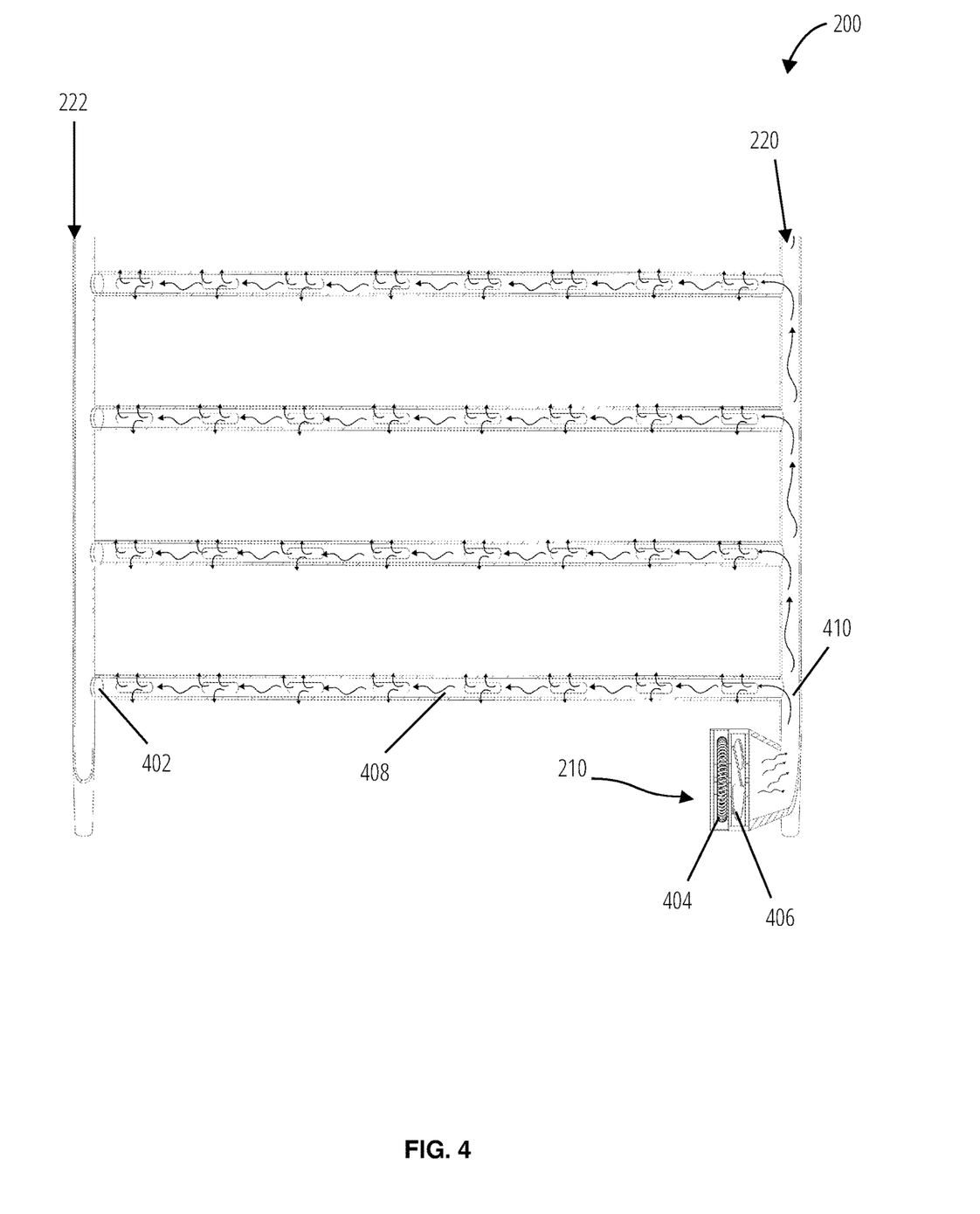
FIG. 4 illustrates a partial sectional view of the heated towel rack 100 in accordance with one embodiment.
Figure 5:
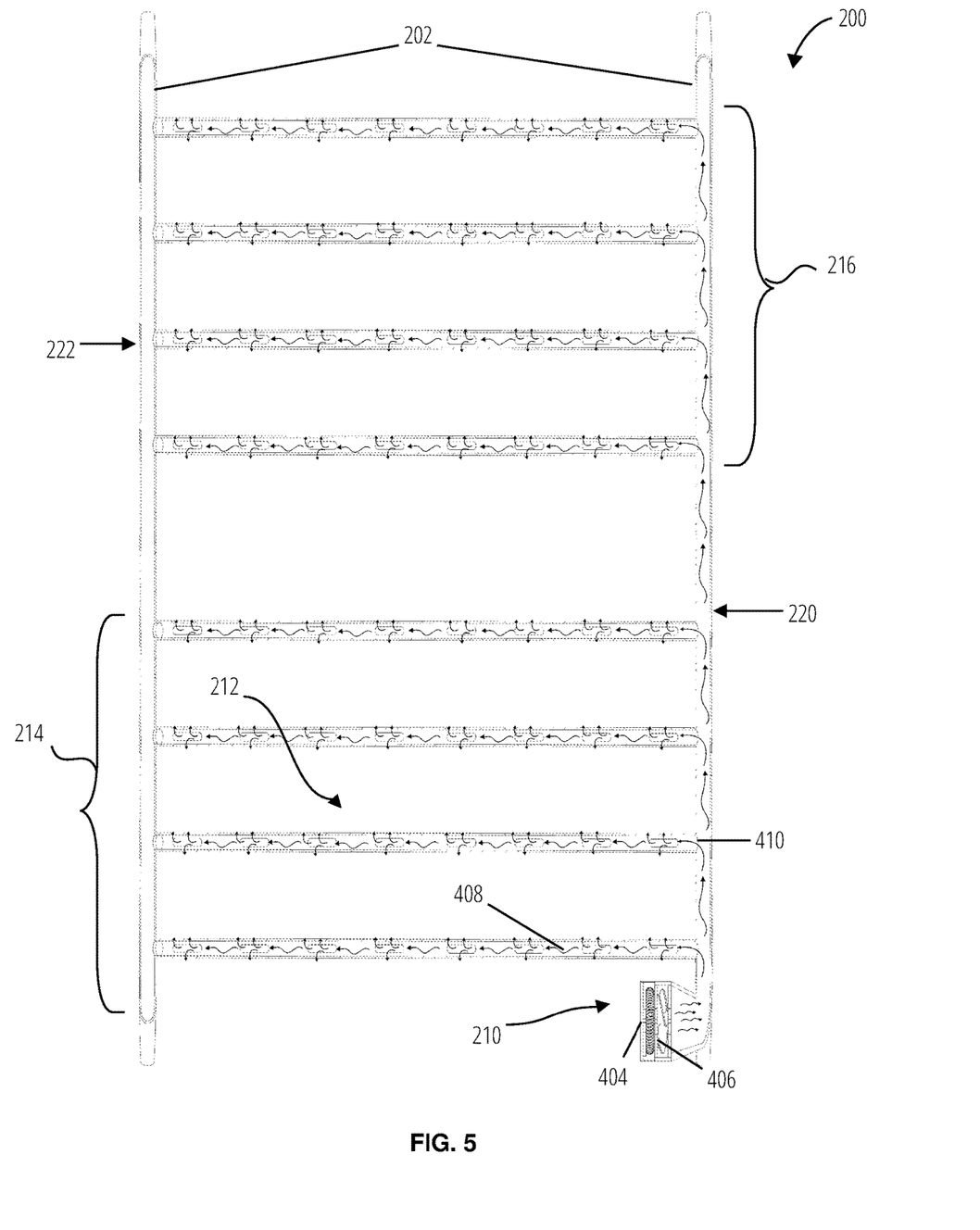
FIG. 5 illustrates a sectional view of the heated towel rack 100 in accordance with one embodiment.

As shown in FIG. 4, the at least two lateral supports 202 include a channel 410 that is in fluid communication with the forced air heating unit 210 and the plurality of cross bars 212. The plurality of cross bars 212 are coupled between the at least two lateral supports 202. Each cross bar of the plurality of cross bars 212 include a conduit 408 that is in fluid communication with the channel 410 of at least one lateral support of the at least two lateral supports 202. Each cross bar of the plurality of cross bars 212 include at least one vent 218 that traverses into the conduit 408. In some embodiments, the cross bar 212 may comprise a plurality of vents, while in other embodiments, the cross bar 212 may comprise a single vent 218 that may extend over a portion of the cross bar 212. The vent(s) 218 act as an exhaust point for heated air from the forced air heating unit 210. The forced air heating unit 210 generates heat and forces air through the channel 410 at least one of the lateral supports 202 and through the vents 218 by way of the conduit 408. FIG. 5 illustrates an exemplary embodiment where the airflow may be directed only through the first lateral support 220, while in other embodiments the airflow could be present in (or directed through) the second lateral support 222 and/or both the first lateral support 220 and the second lateral support 222.

The forced air heating unit 210 forces heated air through the heated towel rack 100. In some configurations, the forced air heating unit 210 may comprise a fan 406 and a heating element 404. The fan 406 creates the air movement for forcing or directing heated air through the channel 410 of a lateral support of the at least two lateral supports 202. The heating element 404 generates heat raising the temperature of the surrounding air that is forced through the heated towel rack 100. In some configurations, the fan 406 may be positioned between the heating element 404 and the channel 410. In alternative configurations, the heating element 404 may be positioned between the fan 406 and the channel 410.

As shown in FIG. 2, the forced air heating unit 210 may be operated utilizing a controller 204 communicating with a user device 208 by way of a wireless communication module 206. A user may operate a user interface through the user device 208 to communicate control signals for changing the temperature and volume of air being pushed out through the plurality of vents 218. The control signals would be received by the controller 204 through a wireless communication module 206 to control the temperature settings of the heating element 404 and the speed of the fan 406. The wireless communication module 206 may communicate wirelessly with the user device 208 through any wireless communications technology including, but not limited to WiFi, near field communications (NFC), Bluetooth, mobile communications standards (e.g., Long Term Evolution (LTE), etc.), and etc. In some configurations, the controller 204 may be accomplished by an electro-mechanical switch that turns the device on/off. The electro-mechanical switch may additionally incorporate a timer mechanism and/or a temperature sensor to control when the forced air heating unit 210 turns on or off. In some embodiments, the controller 204 may be operated via a remote control configured to communicate with the controller 204 via a wireless connection, such as infrared (IR), radio frequency (RF), or another wireless connection. In some embodiments, the controller 204 may be operated via manual manipulation and/or remote manipulation using any of the above described methods.

In some embodiments, the controller 204 may comprise an input for the user to control the temperature of the air that is directed into the towel rack 100 via the forced air heating unit 210. In some embodiments, the heating element 404 may be optionally activated or not activated with the fan 406, depending on if the user wishes for the air directed out of the vents 218 to be heated or room temperature. In some embodiments, the heating element 404 may comprise multiple heat settings, where a user may choose one of a plurality of heat settings via the controller 204 and/or communication with the controller 204.

In some embodiments, the towel rack 100 may comprise a power source 209 configured to power the other elements of the towel rack 100. For example, the power source 209 may comprise battery power, where one or more battery may be connected to a part of the towel rack 100 and in communication with the controller 204 and/or the forced air heating unit 210. The power source 209 may also comprise corded, plug-in, or hard-wired power, where a cord may be connected to a part of the towel rack 100 and in communication with the controller 204 and/or the forced air heating unit 210.

In some configurations, more than one forced air heating unit 210 may be utilized in the heated towel rack. In a two unit arrangement, one forced air heating unit may be positioned on the lower portion of one lateral support, while the other forced air heating unit may be positioned the opposite end of the neighboring lateral support. Alternatively, one or more fans may be positioned on (or within) one or more support cross bar (which may be parallel to cross bars and attached to the lateral supports). In some embodiments, the towel rack may comprise two or more fans positioned on the support cross bars, where each of the multiple fans may direct air flow to only a portion of the cross bars and vents. For example, a first fan may provide airflow to an upper portion of the towel rack (and may be positioned on the upper portion of the towel rack), and a second fan may provide airflow to a lower portion of the towel rack (and may be position on the lower portion of the towel rack).

In some configurations, the forced air heating unit 210 may include more than one heating element 404. In some embodiments, the heating element(s) 404 may be positioned within the conduit 408 and/or within the channel 410 and may be utilized in addition to or as an alternative to the single heating unit configurations that have been previously described. In some embodiments, the fan 406 of the forced air heating unit 210, and/or the entire forced air heating unit 210, may be positioned anywhere on the towel rack 100 that is in fluid communication with the channel 410, the conduit 408, and/or the vents 218. For example, the forced air heating unit 210 may be positioned on one of the support cross bars (described above), wherein the support cross bar(s) may comprise a channel within the support cross bar to provide fluid communication between the forced air heating unit 210 and the rest of the towel rack (i.e., the conduit, channels, and/or vents).

In the example shown in FIG. 2 through FIG. 5, the heated towel rack 100 is configured with a single forced air heating unit 210 positioned on the lower portion of a lateral support. The region proximal to the forced air heating unit 210 is considered the first section 214, while the region distal to the forced air heating unit 210 is considered the second section 216. Similarly, the lateral support coupled to the forced air heating unit 210 is considered the first lateral support 220, while the other lateral support is considered the second lateral support 222.

To help improve airflow from the forced air heating unit 210 through the channel 410 and subsequently the conduit 408 of the plurality of cross bars 212, the conduit 408 of the plurality of cross bars 212 in the second section 216 may be larger than the conduit 408 in the first section 214. Additionally, the plurality of vents 218 in the second section 216 may be larger than the plurality of vents 218 in the first section 214. Through changing the width of either, or in combination, the plurality of vents 218 of the conduit 408, the flow rate and temperature of heated air through the plurality of vents 218 may be consistent across all of the plurality of vents 218. In some embodiments, the number of vents 218 may be different in the first section 214 and the second section 216 to provide consistent air flow to all of the vents 218.

In some embodiments, one or more of the cross bars 212 may comprise vents 218 on the back side of the cross bar 212. In some embodiments, one or more of the cross bars 212 may comprise vents 218 on the front side and/or the back side of the cross bar 212. In some embodiments, one or more of the cross bars 212 may not comprise vents 218 while other cross bars 212 may comprise vents 218. Also, in some embodiments, some cross bars may comprise a greater number of vents than other cross bars.

The heated towel rack 100 may also incorporate at least one stopper 402 to help air flow through the conduit 408 of the plurality of cross bars 212. A stopper 402 is obstructively positioned within a cross bar 212 on the end of the cross bar 212 proximal to the second lateral support 222. In some embodiments, any number of the cross bars 212 may comprise a stopper 402. In some embodiments, one or more of the cross bars 212 may not comprise a stopper to allow for fluid communication between the channels 410 of the lateral supports 220 and 222. In some configurations, more than one forced air heating unit 210 may be incorporated into a heated towel rack, the stopper 402 may not be needed in these configurations. In some configurations, the stopper 402 may be utilized to block portions of the channel 410 within the lateral support that do not interface with the conduit 408. In some configurations, the conduit 408 may taper such that the width of the conduit 408 towards the second lateral support 222 is larger than the width of the conduit 408 proximal to the first lateral support 220.

In some embodiments, one or more elements of the towel rack 100 may comprise a metal material. In some embodiments, one or more elements of the towel rack 100 may comprise a plastic material, such as a thermoplastic, a polymer, and/or another plastic material. In some embodiments, one or more elements of the towel rack 100 may comprise a ceramic material. The material may be selected to prevent damage from heating by the heating elements of the forced air heating unit.

In some embodiments, the towel rack 100 may comprise snap fit components, wherein the towel rack 100 may ship in multiple pieces or components which may then be assembled by a customer. In some embodiments, a front surface or panel (i.e., that faces away from the wall when the towel rack 100 is install onto a wall) may be configured to be replaceable and may comprise a variety of colors or designs. In some embodiments, additional front surfaces or panels may be sold separately from the towel rack 100. This may be useful for a user who has installed the towel rack 100 in their bathroom or other room, and then changes the decorations or design of the room, and then wish to change the appearance of the towel rack 100 to coordinate with the new design.

In some embodiments, the towel rack 100 may be sized to fit or accommodate a particular size of towel or other garment. For example, the towel rack 100 may be sized to fit a bath sheet, a body towel, a hand towel, a washcloth, a robe, or another garment.

Figure 6:
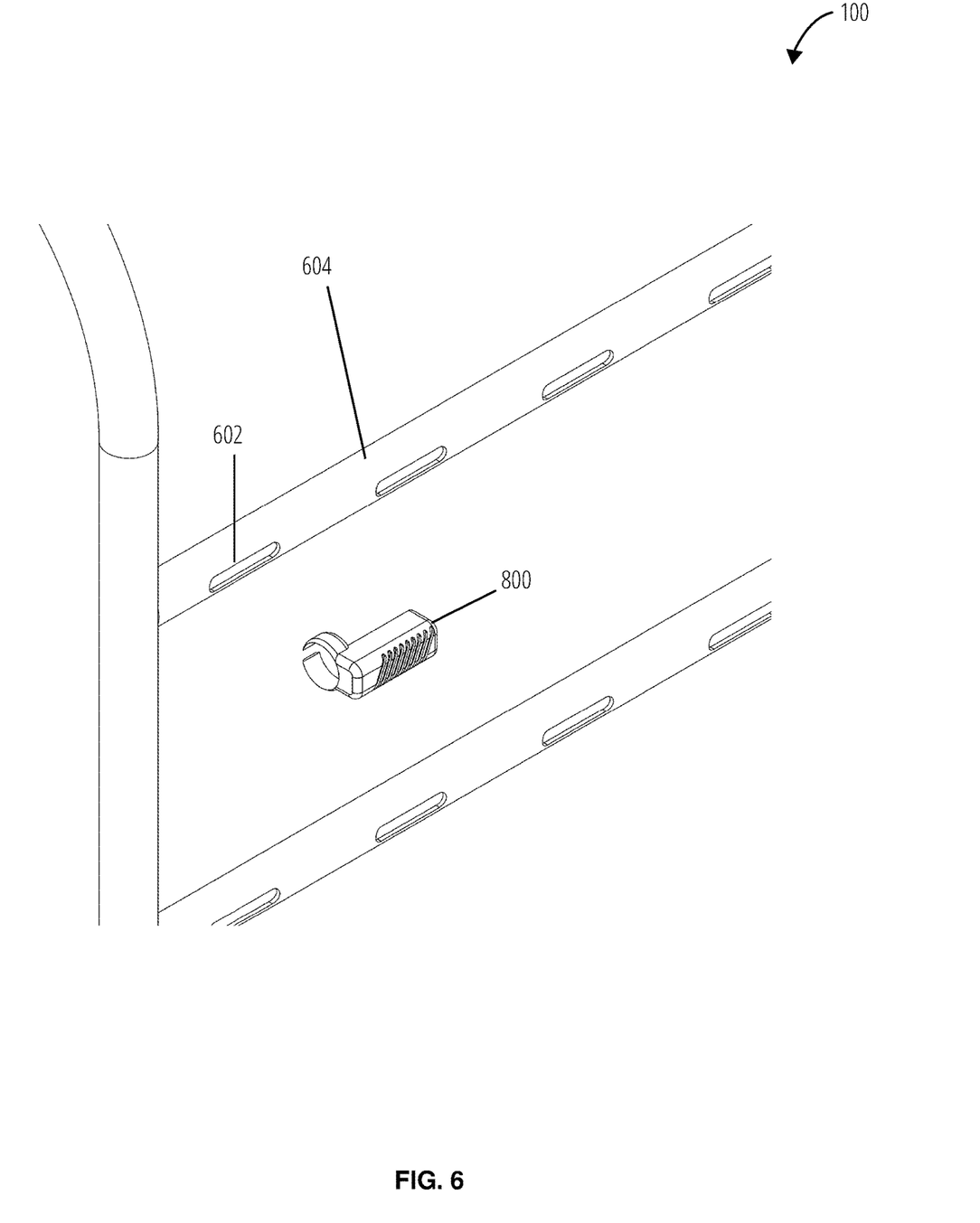
FIG. 6 illustrates a partial isometric view of the heated towel rack 100 in accordance with one embodiment.
Figure 7:
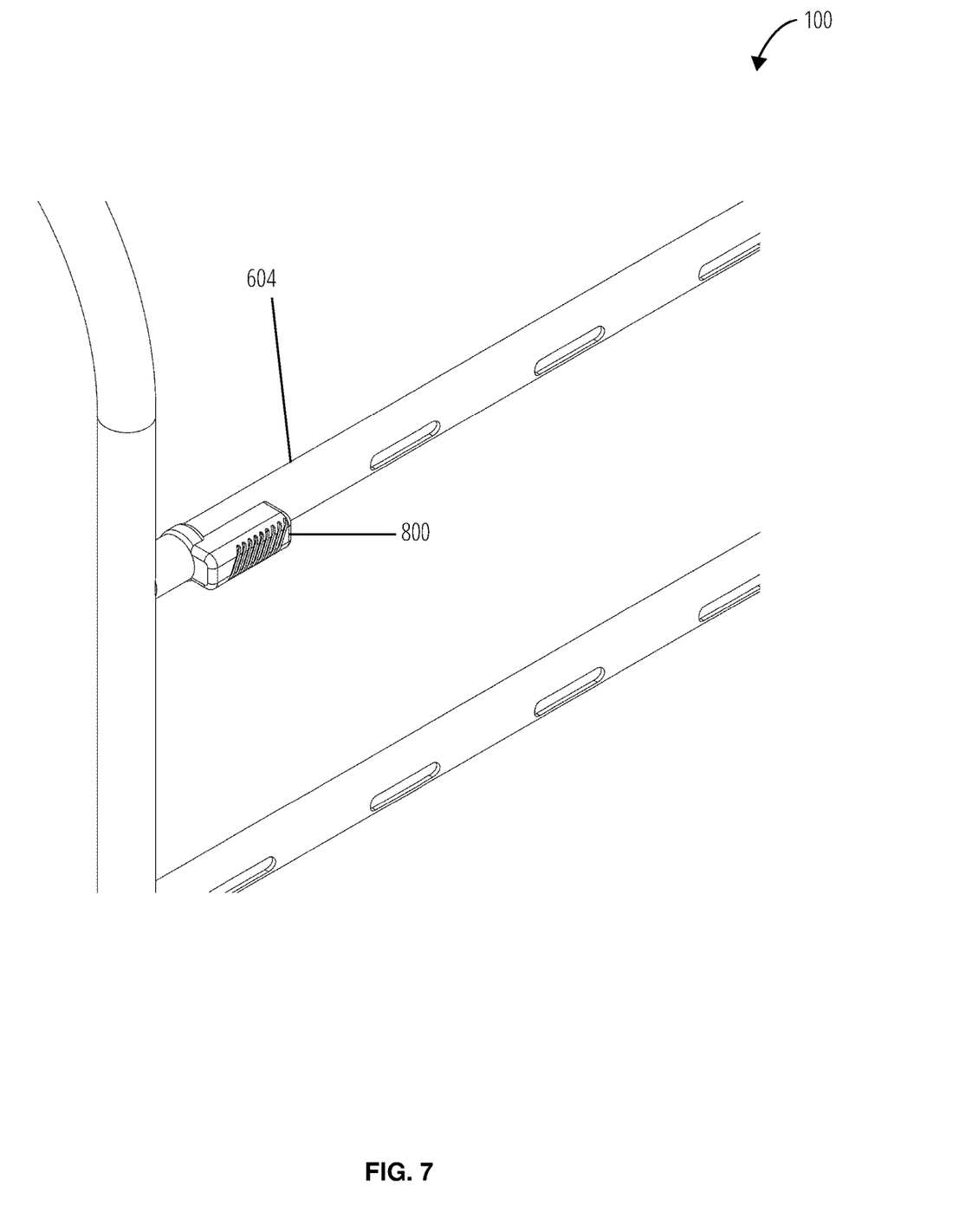
FIG. 7 illustrates a partial isometric view of the heated towel rack 100 in accordance with one embodiment.
Figure 8:
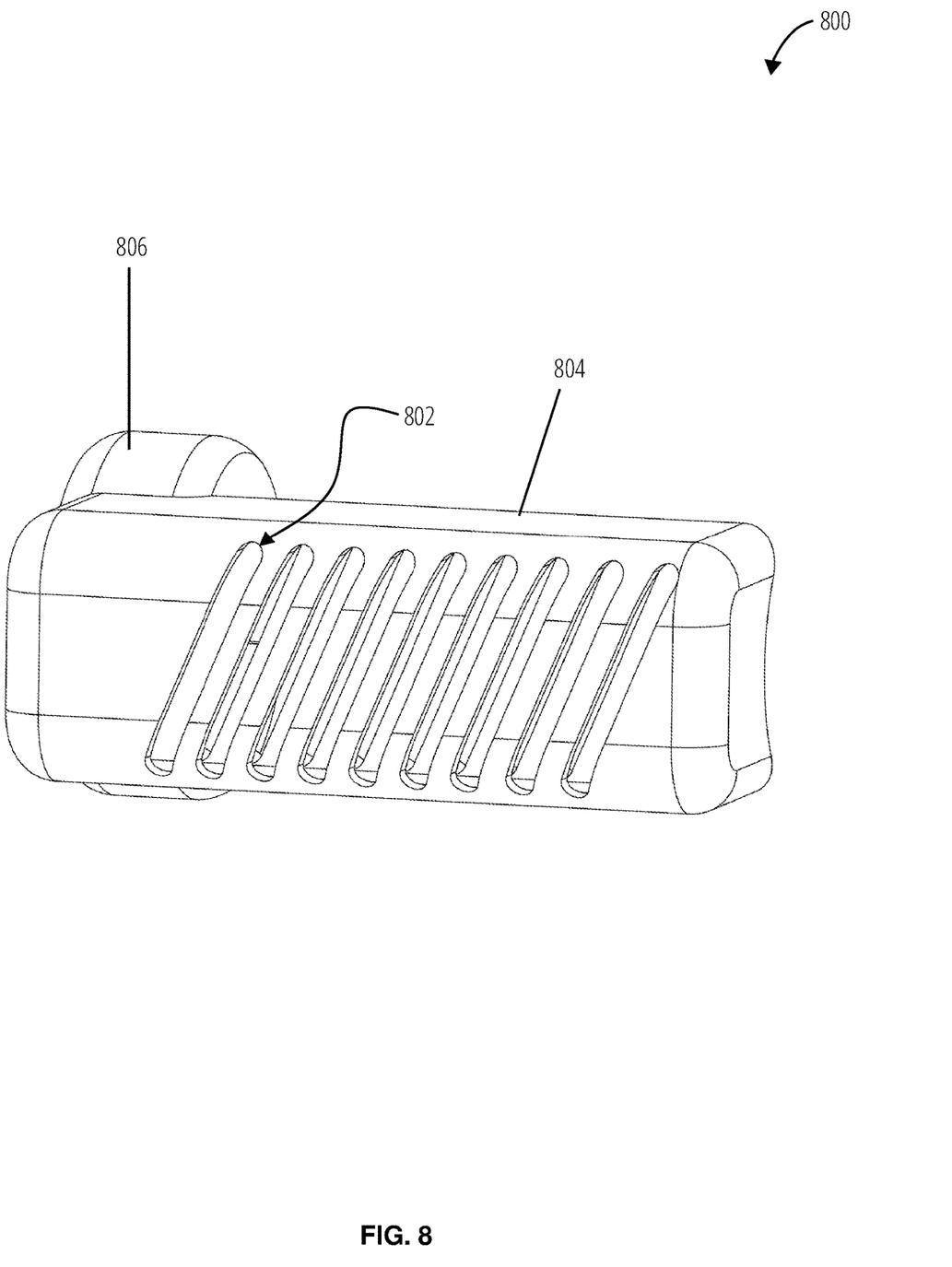
FIG. 8 illustrates a perspective view of an attachable aroma therapy element 600 in accordance with one embodiment.

Referencing FIG. 6 through FIG. 8, an attachable aroma therapy element 600 may couple over at least one vent 218 on a cross bar 212 of the heated towel rack 100 allowing a scented compound to be released with the heated air that exits the vent 218. As shown in FIG. 8, the attachable aroma therapy element 600 comprises a plurality of slots 802, a housing 804, and a clip 806. The plurality of slots 802 traverse through the housing 804 creating a passage for heated air to exit when the attachable aroma therapy element 600 is placed over a vent 218. In other words, the slots 802 may extend through to the back surface of the vent 218. The housing 804 holds the scented compound in place allowing heated air from the vent 218 to pass through the plurality of slots 802 and carrying the scented compound into the surrounding space. The scented compound may be configured as a disposable insert. The clip 806 functions as the attachment mechanism for securing the attachable aroma therapy element 600 to the cross bar 212. The clip 806 may couple to the cross bar 212 adjacent to the vent 218 to allow the plurality of slots 802 to align with the vent 218.

Figure 1:
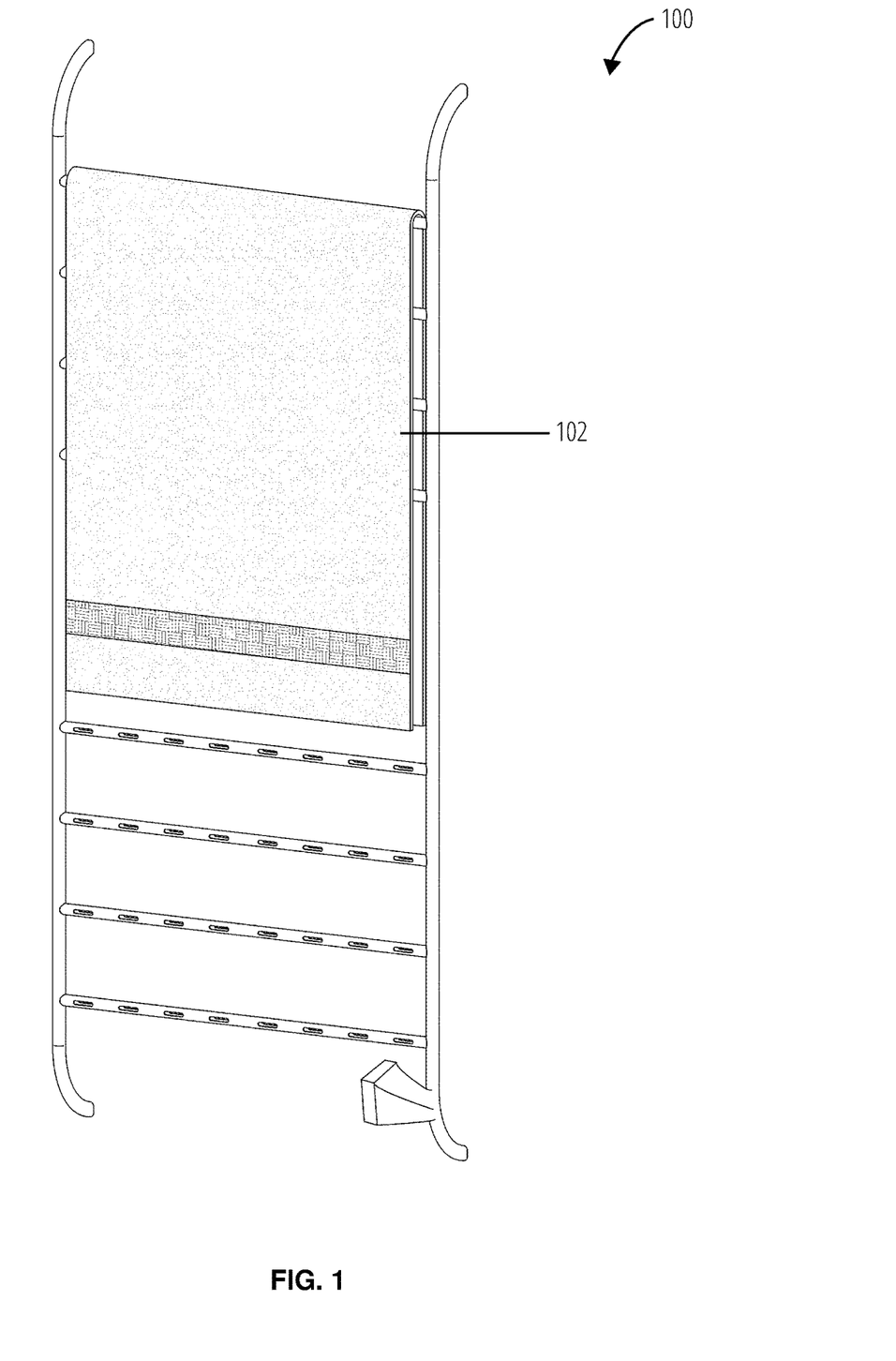
FIG. 1 illustrates a perspective view of a heated towel rack 100 with a towel, in accordance with one embodiment.
Figure 9:
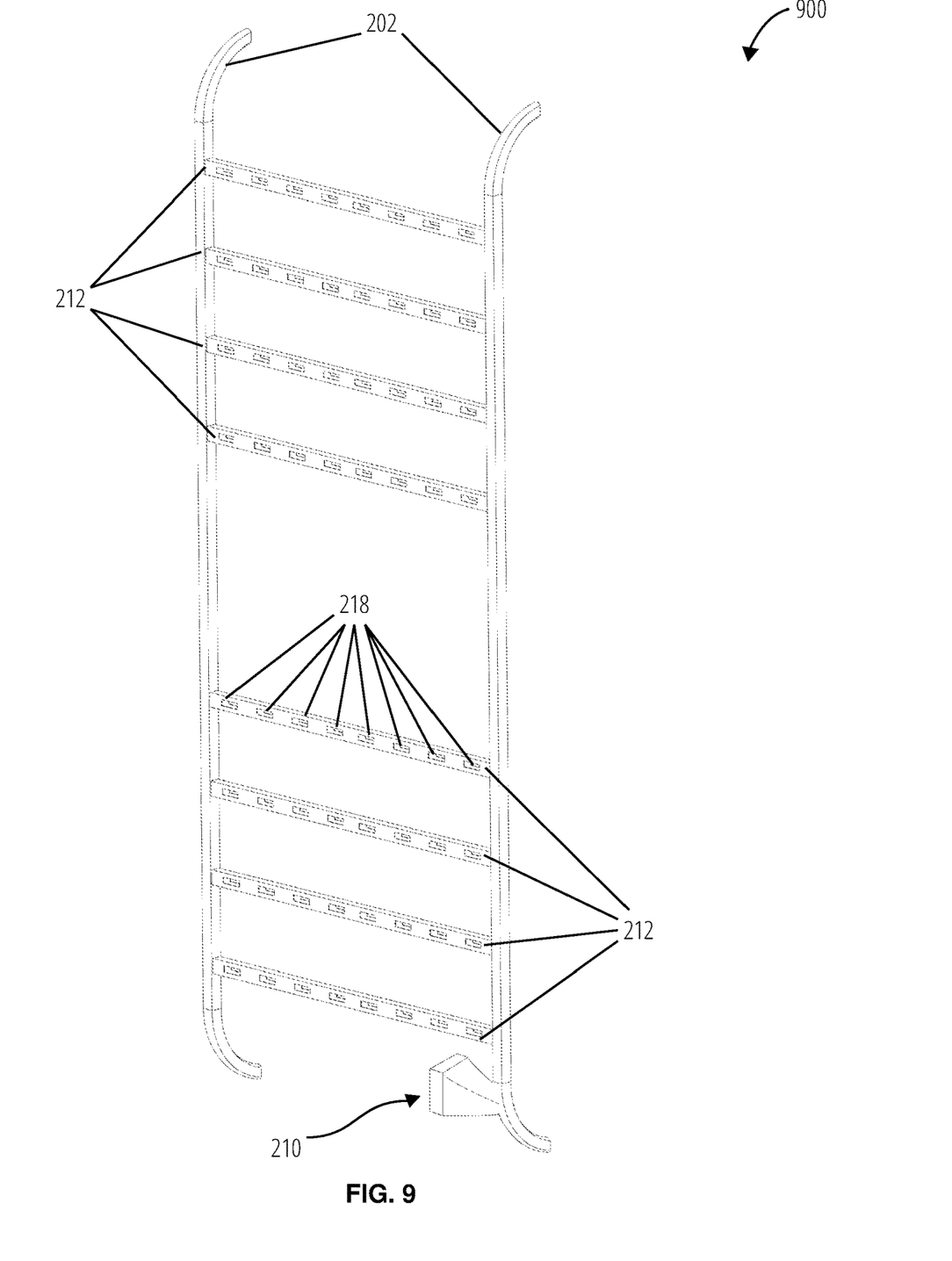
FIG. 9 illustrates a perspective view of a heated towel rack 900 in accordance with one embodiment.

Referencing FIG. 9, a heated towel rack 900 is an alternative configuration of the heated towel rack 100 (as shown in FIG. 1) with the plurality of cross bars 912 being rectangularly shaped such that they have a rectangular profile. The heated towel rack 900 comprises a forced air heating unit 210, at least two lateral supports 202, and a plurality of cross bars 912. In the heated towel rack 100 shown in FIG. 1, the plurality of cross bars 212 are generally cylindrical in shape with the plurality of vents 218 having a semi elliptical profile. In the heated towel rack 900, the plurality of cross bars 912 of the heated towel rack 900 are rectangular in shape. The plurality of vents 218 of the plurality of cross bars 912 may have a rectangular profile. In some configurations, the plurality of vents 218 may have any shape profile (e.g., elliptical, tear drop, etc.) to vent the forced heated air.

The term "wireless communication" in this context refers to the transfer of information between two or more points that are not connected by an electrical conductor. Common wireless technologies use electromagnetic wireless telecommunications, such as radio. With radio waves distances can be short, such as a few meters for television, or as far as thousands or even millions of kilometers for deep-space radio communications. Wireless communication encompasses various types of fixed, mobile, and portable applications, including two-way radios, cellular telephones, personal digital assistants (PDAs), and wireless networking. Other examples of applications of radio wireless technology include GPS units, garage door openers, wireless computer mice, keyboards and headsets, headphones, radio receivers, satellite television, broadcast television and cordless telephones. Less common methods of achieving wireless communications include the use of light, sound, magnetic, or electric fields.

The term "user interface" in this context refers to logic to receive signals from device inputs such as a mouse, keyboard, or microphone, and to correlate those inputs with visual features rendered on an optical display. A user interface determines how a human operator interacts with and controls a device. User interfaces are comprised of elements with which the human operator interacts to affect device behavior. Examples of user interface elements are (1) command language (text): the operator inputs program-specific instructions or codes into the device, (2) menus: the operator selects elements from displayed lists, (3) buttons: the operator selects (typically by clicking the mouse cursor on) defined areas of the display.

Having described various devices and methods herein, exemplary embodiments or aspects can include, but are not limited to:

In a first embodiment, a heated towel rack may comprise at least one lateral support; at least one forced air heating unit in fluid communication with a channel within the lateral support; at least one cross bar coupled to the at least one lateral support; wherein the at least one cross bar comprises at least one vent that traverses into a conduit within the cross bar; and wherein the channel of the lateral support is in fluid communication with the at least one vent by way of the conduit of the cross bar.

A second embodiment can include the heated towel rack of the first embodiment, comprising a plurality of lateral supports.

A third embodiment can include the heated towel rack of the first or second embodiments, comprising a plurality of vents.

A fourth embodiment can include the heated towel rack of any of the first through third embodiments, wherein the at least one forced air heating unit comprises at least one heating element, a fan, and a controller, and wherein the controller is operatively coupled to the at least one heating element and the fan to control air temperature and flow through the plurality of vents.

A fifth embodiment can include the heated towel rack of any of the first through fourth embodiments, further comprising a first lateral support and a second lateral support, wherein the at least one forced air heating unit is coupled to the first lateral support.

A sixth embodiment can include the heated towel rack of the fifth embodiment, wherein at least one stopper is obstructively positioned within the conduit proximal to the second lateral support.

A seventh embodiment can include the heated towel rack of the fifth or sixth embodiment, comprising a plurality of cross bars and further comprising a plurality of stoppers obstructively positioned with conduits of each of the plurality of cross bars proximal to the second lateral support.

In some embodiments, the conduit tapers towards the first lateral support.

An eighth embodiment can include the heated towel rack of any of the first through seventh embodiments, wherein the at least two lateral supports comprises a first section and a second section; wherein the first section is proximal to the at least one forced air heating unit; wherein the second section is distal to the at least one forced air heating unit; and wherein a conduit of a cross bar in the second section is larger than a conduit of a cross bar in the first section.

A ninth embodiment can include the heated towel rack of any of the first through eighth embodiments, further comprising an attachable aroma therapy element comprising a clip, a housing, a plurality of slots, and a scented compound, wherein the scented compound is positioned within the housing, wherein the plurality of slots traverse the housing, wherein the attachable aroma therapy element being coupled to the cross bar adjacent to a vent of the plurality of vents by way of the clip, and wherein the plurality of slots are operatively aligned with the vent.

A tenth embodiment can include the heated towel rack of any of the first through eighth embodiments, comprising a plurality of cross bars.

In some embodiments, the plurality of cross bars are cylindrically shaped.

In some embodiments, the plurality of cross bars are rectangularly shaped.

In some embodiments, at least two of the plurality of cross bars comprise at least one vent.

In an eleventh embodiment, a method for assembling a towel drying rack may comprise connecting one or more lateral supports to a plurality of cross bars; fluidly connecting a channel within at least one of the lateral supports to conduit within each of the plurality of cross bars; fluidly connecting the conduit with at least one vent formed into the cross bars, wherein the at least one vent is configured to direct airflow out of the towel drying rack; and fluidly connecting a forced air unit to at least one of the channel and the conduit.

A twelfth embodiment can include the method of the eleventh embodiment, further comprising directing airflow, by the forced air unit, into the channel within the at least one lateral support; directing airflow from the channel into the plurality of conduits positioned within the plurality of cross bars attached to the lateral support element; and directing airflow from the conduits out of the at least one vent in the cross bars toward a towel or other garment.

A thirteenth embodiment can include the method of any of the eleventh or twelfth embodiments, further comprising fluidly connecting one or more heating elements to one or more of the forced air unit, the conduit, and the channel.

A fourteenth embodiment can include the method of the thirteenth embodiment, further comprising heating airflow generated by the forced air unit before the airflow exits the at least one vent of the cross bars.

A fifteenth embodiment can include the method of any of the eleventh through fourteenth embodiments, further comprising: connecting a controller to one or more of the elements of the towel rack; and manually or remotely controlling the operation of the towel rack via the controller.

A sixteenth embodiment can include the method of any of the eleventh through fifteenth embodiments, further comprising attaching one or more aroma therapy element over one or more of the vents of the cross bars.

In a seventeenth embodiment, a garment drying rack may comprise at least one lateral support comprising a channel within the interior of the lateral support; at least one forced air unit in fluid communication with the channel within the lateral support configured to generate airflow into the channel; at least one cross bar comprising a conduit positioned within the interior of the cross bar, wherein the conduit is in fluid communication with the channel; and a plurality of vents in fluid communication with the conduit, the channel being in fluid communication with the plurality of vents by way of the conduit.

An eighteenth embodiment can include the garment drying rack of the seventeenth embodiment, further comprising one or more heating elements in fluid communication with one or more of the forced air unit, the conduit, and the channel, the heating elements configured to heat the airflow before it exits the vents.

A nineteenth embodiment can include the garment drying rack of the seventeenth or eighteenth embodiments, further comprising at least one aroma therapy element positioned over at least one of the vents configured to provide a scent that is spread via the airflow exiting the vent.

A twentieth embodiment can include the garment drying rack of any of the seventeenth through nineteenth embodiments, wherein the rack is sized to fit a particular garment to be dried.

In some embodiments, the garment drying rack may comprise a first cross bar, a second cross bar, and a third cross bar. In some embodiments, the garment drying rack may comprise a first vent, a second vent, and a third vent.

What is claimed is:

1. A heated towel rack comprising:
   a first section, wherein the first section comprises a plurality of first section cross bars coupled thereto and wherein each of the plurality of first section cross bars comprise a first section cross bar conduit;
   at least one first section vent, wherein the at least one first section vent traverses the first section cross bar conduit of at least one of the plurality of first section cross bars;
   a second section, wherein the second section comprises a plurality of second section cross bars coupled thereto and wherein each of the plurality of second section cross bars comprise a second section cross bar conduit;
   at least one second section vent, wherein the at least one second section vent traverses the second section cross bar conduit of at least one of the plurality of second section cross bars;
   a plurality of lateral supports, wherein the first section and the second section are fluidly connected via the plurality of lateral supports;
   at least one forced air heating unit in fluid communication with a channel within the plurality of lateral supports;
   wherein the channel within the plurality of lateral supports is in fluid communication with the at least one first section vent, the at least one second section vent, or combinations thereof, and wherein the second section cross bar conduit is larger than the first section cross bar conduit.

2. The heated towel rack of claim 1, wherein the at least one forced air heating unit comprises at least one heating element, a fan, and a controller, and wherein the controller is operatively coupled to the at least one heating element and the fan to control air temperature and flow through the at least one vent.

3. The heated towel rack of claim 1, wherein the plurality of lateral supports comprise a first lateral support and a second lateral support, wherein the at least one forced air heating unit is coupled to the first lateral support.

4. The heated towel rack of claim 3, wherein at least one stopper is obstructively positioned within the conduit proximal to the second lateral support.

5. The heated towel rack of claim 3, comprising a plurality of stoppers obstructively positioned within at least one first section cross bar conduit, at least one second section cross bar conduit, or combinations thereof, and proximal to the second lateral support.

6. The heated towel rack of claim 1, further comprising an attachable aroma therapy element comprising a clip, a housing, at least one slot, and a scented compound, wherein:
   the scented compound is positioned within the housing;
   the at least one slot traverses the housing;
   the attachable aroma therapy element is coupled to at least one of the plurality of first section cross bars or to at least one of the plurality of first section cross bars adjacent to at least one first section vent or at least one second section vent by way of the clip; and
   the at least one slot is operatively aligned with the at least one first section vent or the at least one second section vent.

7. The heated towel rack of claim 1, wherein at least two of the plurality of first section cross bars comprise at least one first section vent, at least two of the plurality of second section cross bars comprise at least one second section vent, or combinations thereof.

8. A method for assembling a towel drying rack, the method comprising:

connecting one or more lateral supports to a plurality of cross bars, wherein a first portion of the plurality of cross bars constitutes a first section of the towel drying rack, and wherein a second portion of the plurality of cross bars constitutes a second section of the towel drying rack, and wherein a second section cross bar conduit is larger than a first section cross bar conduit;

fluidly connecting a channel within at least one of the lateral supports to at least one first section cross bar conduit and at least one second section cross bar conduit;

fluidly connecting least one vent formed into at least one of the plurality of cross bars to at least one first section cross bar conduit or at lea one second section cross bar conduit, wherein the at least one vent is configured to direct airflow out of the towel drying rack; and fluidly connecting a forced air unit to at least one of the channel within at least one of the lateral supports, at least one first section cross bar conduit, and at least one second section cross bar conduit.

9. The method of claim 8, further comprising:

directing airflow, by the forced air unit, into the channel within the at least one of the lateral supports;

directing airflow from the channel into the at least one first section cross bar conduit, the at least one second section cross bar conduit, or combinations thereof; and directing airflow from the at least one first section cross bar conduit, the at least one second section cross bar conduit, or combinations thereof out of the at least one vent formed into at least one of the plurality of cross bars toward a towel or other garment.

10. The method of claim 8, further comprising fluidly connecting one or more heating elements to one or more of the forced air unit, each conduit of the plurality of cross bars, and the channel.

11. The method of claim 10, further comprising heating airflow generated by the forced air unit before the airflow exits the at least one vent formed into at least one of the plurality of cross bars.

12. The method of claim 8, further comprising:

connecting a controller to one or more of the elements of the towel drying rack; and manually or remotely controlling the operation of the towel drying rack via the controller.

13. The method of claim 8, further comprising attaching an aroma therapy element over at least one vent formed into the at least one of the plurality of cross bars.

14. A garment drying rack comprising:

at least one lateral support comprising a channel within an interior of the lateral support;

at least one forced air unit in fluid communication with the channel within the lateral support configured to generate airflow into the channel;

a plurality of cross bars, wherein each of the plurality of cross bars comprise a conduit positioned within an interior of each of the plurality of cross bars, wherein the conduit of each of the plurality of cross bars is in fluid communication with the channel, wherein a first portion of the plurality of cross bars constitutes a first section of the garment drying rack, and wherein a second portion of the plurality of cross bars constitutes a second section of the garment drying rack, and wherein a second section cross bar conduit is larger than a first section cross bar conduit; and a plurality of vents, wherein at least a first vent of the plurality of vents is in fluid communication with a first conduit of one of the plurality of cross bars and wherein at least a second vent of the plurality of vents is in fluid communication with a second conduit of one of the plurality of cross bars.

15. The garment drying rack of claim 14, further comprising one or more heating elements in fluid communication with one or more of the forced air unit, the conduit positioned within the interior of each of the plurality of cross bars, and the channel, the heating elements configured to heat the airflow before it exits the plurality of vents.

16. The garment drying rack of claim 14, further comprising at least one aroma therapy element positioned over at least one vent of the plurality of vents configured to provide a scent that is spread via the airflow exiting the at least one of the plurality of vents.

* * * * *